(12) United States Patent
Wu et al.

(10) Patent No.: US 8,067,568 B2
(45) Date of Patent: Nov. 29, 2011

(54) METHOD FOR DIAGNOSING SPINAL MUSCULAR ATROPHY

(75) Inventors: Shou-Mei Wu, Kaohsiung (TW); Chun-Chiu Wang, Kaohsiung (TW); Jan-Gowth Chang, Kaohsiung (TW); Yuh-Jyh Jong, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 12/910,849

(22) Filed: Oct. 24, 2010

(65) Prior Publication Data
US 2011/0033861 A1 Feb. 10, 2011

Related U.S. Application Data

(62) Division of application No. 12/497,900, filed on Jul. 6, 2009, now Pat. No. 7,875,432.

(30) Foreign Application Priority Data

Mar. 16, 2009 (TW) .............................. 98108379 A

(51) Int. Cl.
*C07H 21/04* (2006.01)
(52) U.S. Cl. ..................... 536/24.33; 536/23.3; 435/975
(58) Field of Classification Search .................... None
See application file for complete search history.

*Primary Examiner* — Christopher M. Babic
(74) *Attorney, Agent, or Firm* — Pai Patent & Trademark Law Firm; Chao-Chang David Pai

(57) ABSTRACT

A method for diagnosing spinal muscular atrophy is provided. The method includes providing a biological sample of a subject containing a nucleotide of SMN gene, amplifying SMN exons 1, 2*a*, 2*b*, 3, 4, 5, 6, 7, and 8 by a universal multiplex PCR using the nucleotide as a template and the primers to obtain fragments of the SMN exons 1, 2*a*, 2*b*, 3, 4, 5, 6, 7, and 8, labeling the fragments of the SMN exons 1, 2*a*, 2*b*, 3, 4, 5, 6, 7, and 8 by a fluorescent primer to obtain fluorescence-labeled exon fragments, and analyzing the fluorescence-labeled exon fragments by a capillary electrophoresis. If the SMN1/SMN2 ratios in exon 7 and 8 are different, it indicates that the subject is susceptible to spinal muscular atrophy. Additionally, if the peak of certain exon fragment appears crossed, it indicates an intragenic mutation in the exon.

3 Claims, 9 Drawing Sheets

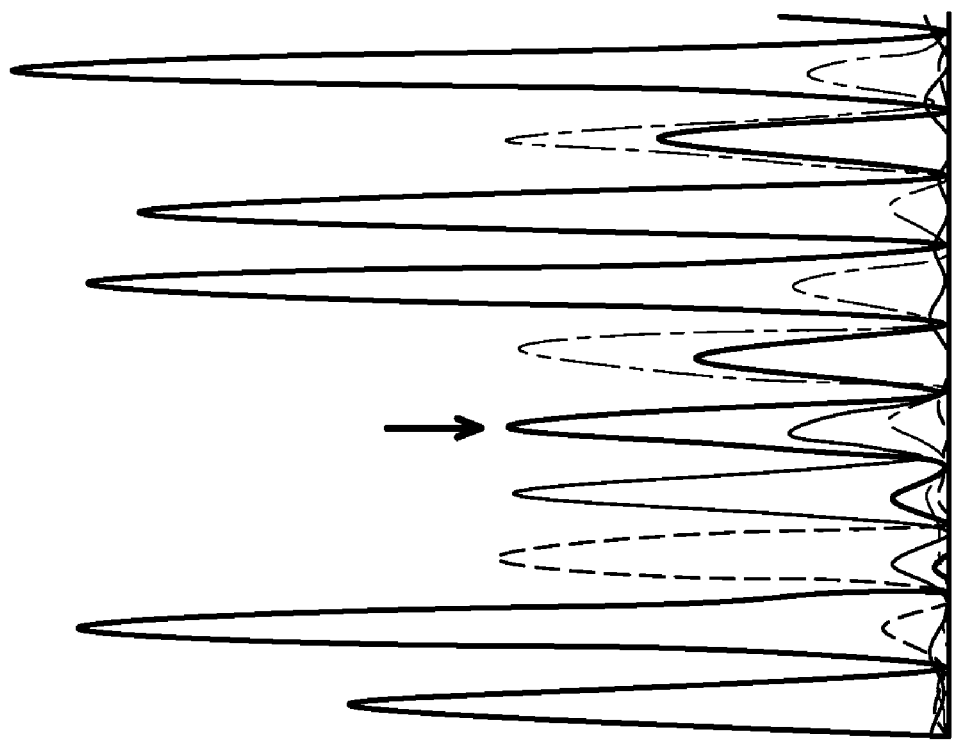

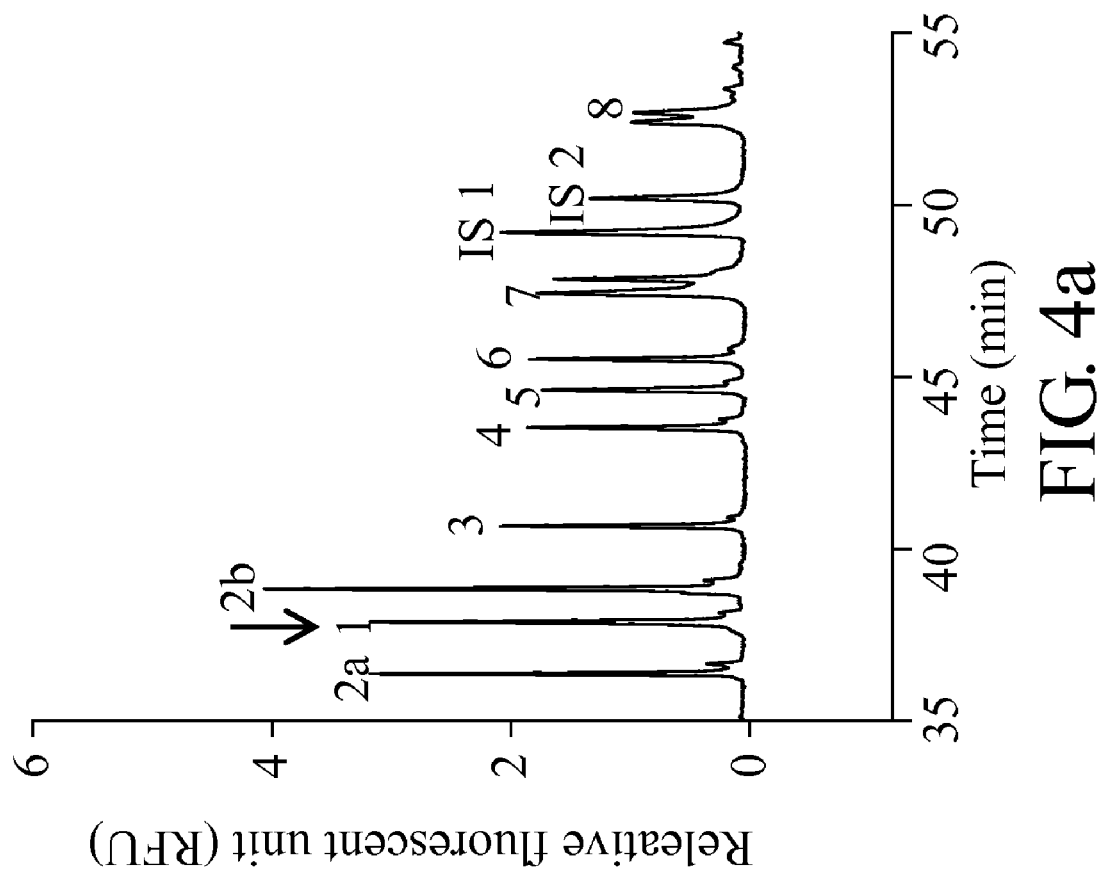

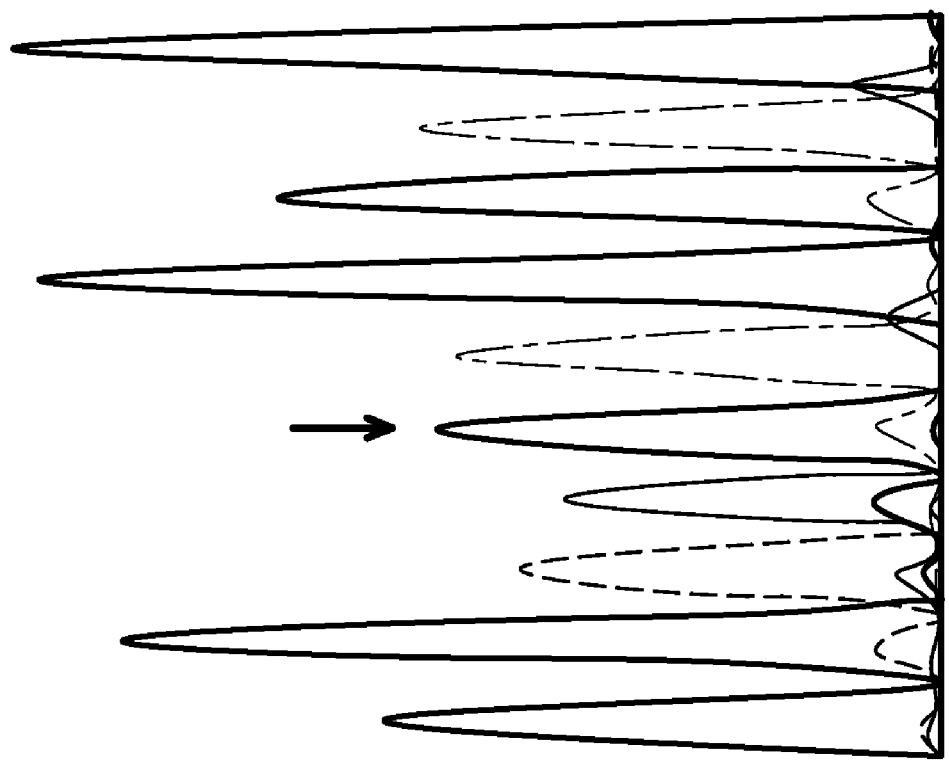

METHOD FOR DIAGNOSING SPINAL MUSCULAR ATROPHY

CROSS REFERENCE TO RELATED APPLICATIONS

The present application is a division of prior U.S. application Ser. No. 12/497,900 filed Jul. 6, 2009, entitled "METHOD FOR DIAGNOSING SPINAL MUSCULAR ATROPHY", from which U.S. Pat. No. 7,875,432 issued on Jan. 25, 2011. The prior U.S. Application claims priority of Taiwan Patent Application No. 98108379, filed on Mar. 16, 2009, the entirety of which is incorporated by reference herein.

BACKGROUND OF THE INVENTION

1. Field of the Invention

The present invention relates to diagnosis of spinal muscular atrophy, and in particular relates to a method for diagnosing spinal muscular atrophy by capillary electrophoresis.

2. Description of the Related Art

Spinal muscular atrophy (SMA) is an autosomal recessive disease characterized by degeneration of motor neurons in the anterior horn of a spinal cord, leading to muscular paralysis and atrophy. SMA is traditionally categorized into three types, according to the age and severity. For children with SMA, SMA is categorized as: type I, severe; type II, intermediate; and type III, mild. For adults with mild symptoms of SMA, SMA is categorized as type IV. Additionally, for prenatal onset of very severe symptoms of SMA and early neonatal death due to SMA, SMA is categorized as type 0 (Eur J Paediatr Neurol 1999; 3:49-51; Lancet 1995; 346:1162; Neuromuscul Disord 1992; 2:423-428). SMA occurs in approximately 1 in 6000-10000 live births and has a carrier frequency of 1 in 50. It is the second most common autosomal recessive inherited disorder in humans and the most common genetic cause of infant mortality (Semin Neurol 1998; 18:19-26).

SMA is caused by the homozygous deletion or mutations of the survival motor neuron gene (SMN) including telomeric SMN (SMN1) and centromeric SMN (SMN2) genes. The genes possess two differences, which are substitution of single nucleotides in exon 7 (c 840 C>T) and 8 (G>A) in the cDNAs. Deletion of the SMN1 gene has been reported in approximately 94% of clinically typical SMA-affected patients, and the SMN2 copy number has been found to be related to the disease severity and life length. To diagnose SMA, most techniques quantify the nucleotide difference in exon 7 of SMN1/SMN2. However, it has been found that the SMA in approximate 6% of affected patients, is caused by point mutations at other exons in which SMN1 is present. Therefore, only detection of the difference of SMN1/SMN2 genes in exon 7 could not accurately diagnose the SMA disease in a clinical environment.

Thus, to improve the diagnostic accuracy of the SMA disease in a clinical environment, a novel diagnostics method and diagnosis kit is required.

BRIEF SUMMARY OF THE INVENTION

The invention provides a method for diagnosing spinal muscular atrophy, comprising: (a) providing a biological sample comprising a nucleotide containing SMN gene, wherein the biological sample is obtained from a subject; (b) providing primers for SMN exons 1, 2a, 2b, 3, 4, 5, 6, 7, and 8; (c) amplifying SMN exons 1, 2a, 2b, 3, 4, 5, 6, 7, and 8 by a universal multiplex PCR using the nucleotide as a template and the primers to obtain fragments of the SMN exons 1, 2a, 2b, 3, 4, 5, 6, 7, and 8; (d) labeling the fragments of the SMN exons 1, 2a, 2b, 3, 4, 5, 6, 7, and 8 by a fluorescent primer to obtain fluorescence-labeled exon fragments, and (e) analyzing the fluorescence-labeled exon fragments by a capillary electrophoresis, wherein different SMN1/SMN2 ratios in exon 7 and 8 indicates that the subject is susceptible to spinal muscular atrophy.

The invention also provides a kit of for assaying a sample from a subject to detect susceptibility of spinal muscular atrophy, comprising: at least one primer pairs selected from a group consisting of: SEQ ID NOs: 1-2, 3-4, 5-6, 7-8, 9-10, 11-12, 13-14, 15-16, and 17-18; and a user instruction.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein:

FIGS. 3a-3b show results of a capillary electrophoresis analysis and DNA sequencing of an SMA patient bearing one copy of SMN1 and a c.22_23insA mutation in exon 1;

FIGS. 4a-4b show results of a capillary electrophoresis analysis and DNA sequencing of a healthy subject.

DETAILED DESCRIPTION OF THE INVENTION

Figure 1B:
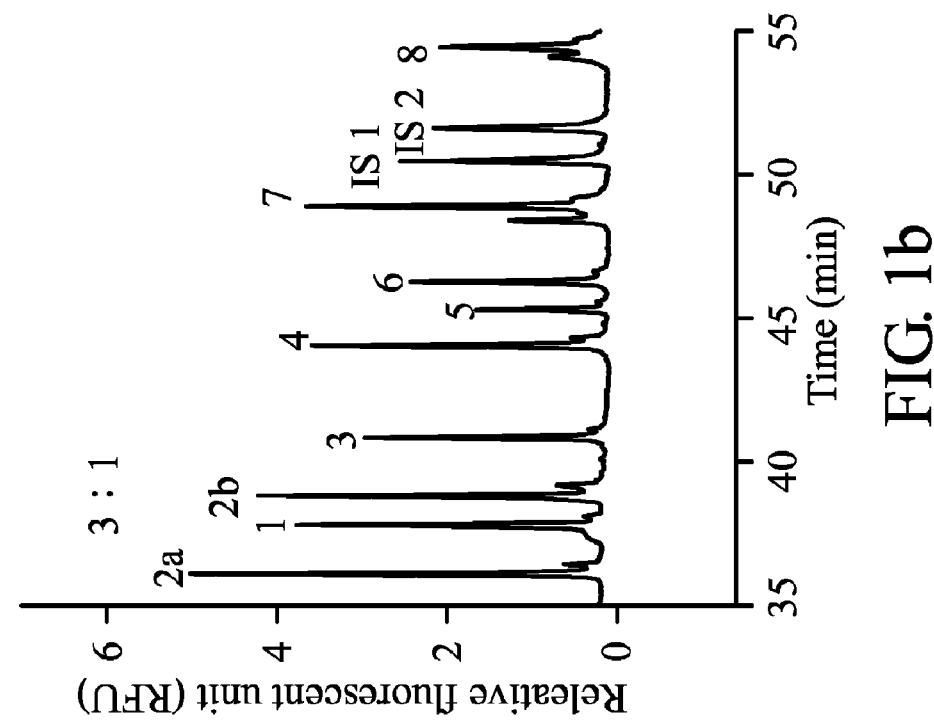
FIGS. 1a-1h show various ratios of SMN1-SMN2 in exon 7 and 8 by a capillary electrophoresis analysis.
Figure 1A:
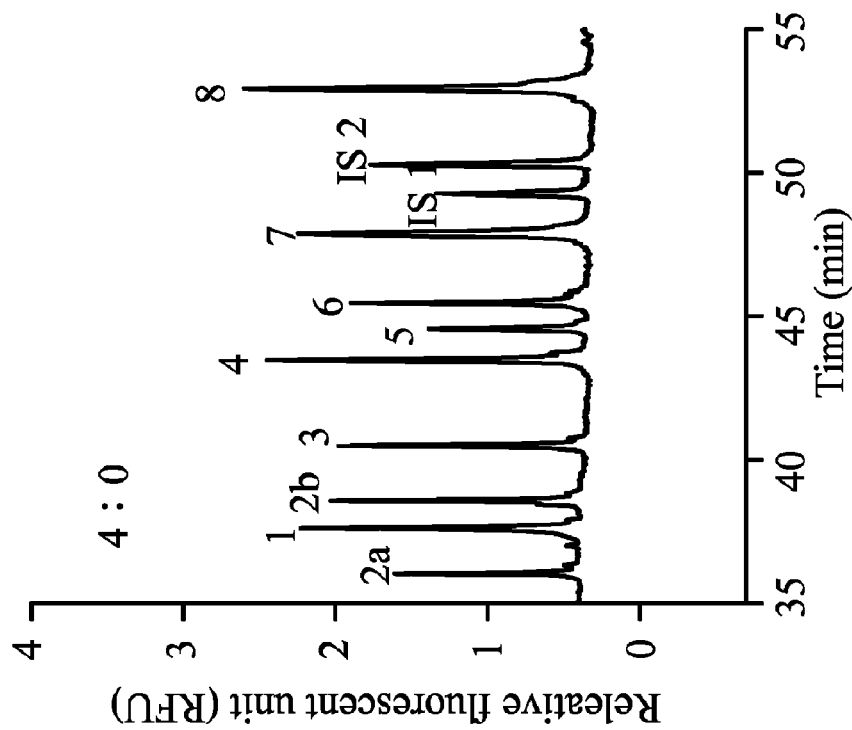
Figure 1C:
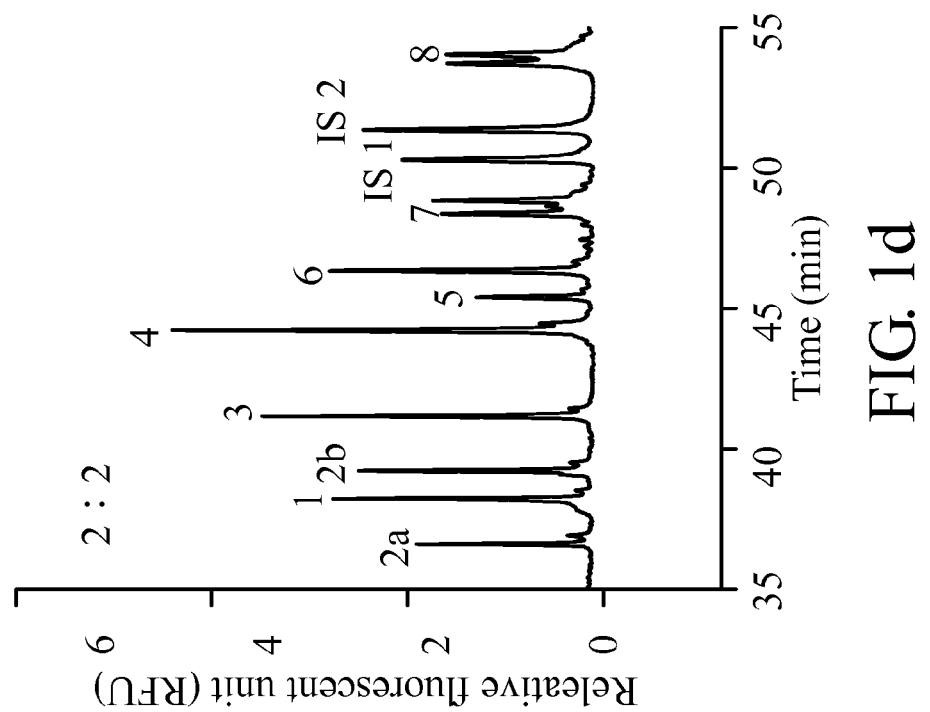
Figure 1D:
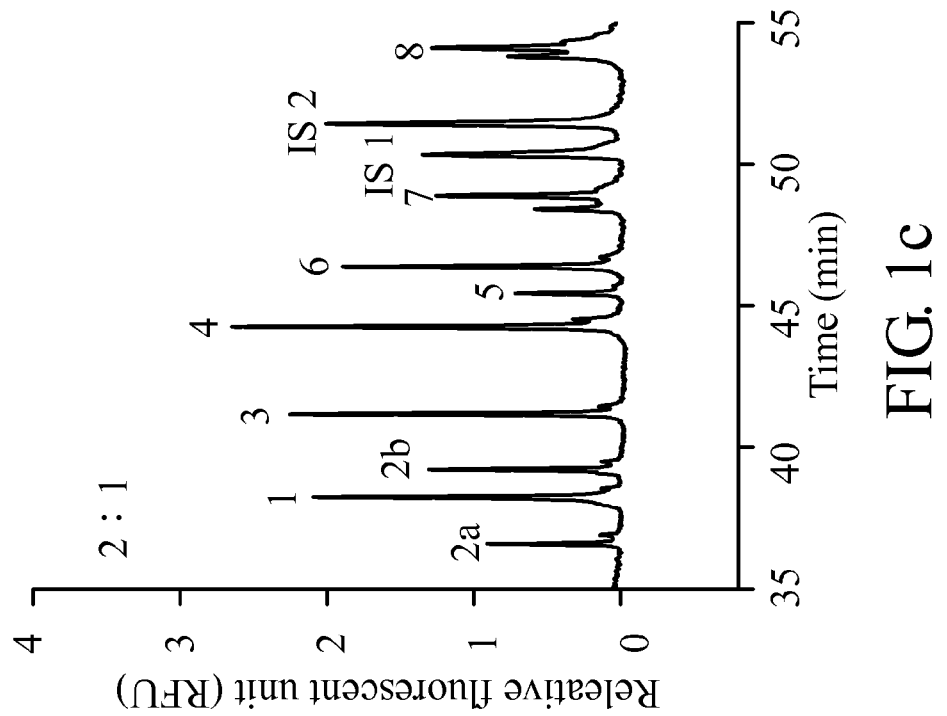
Figure 1E:
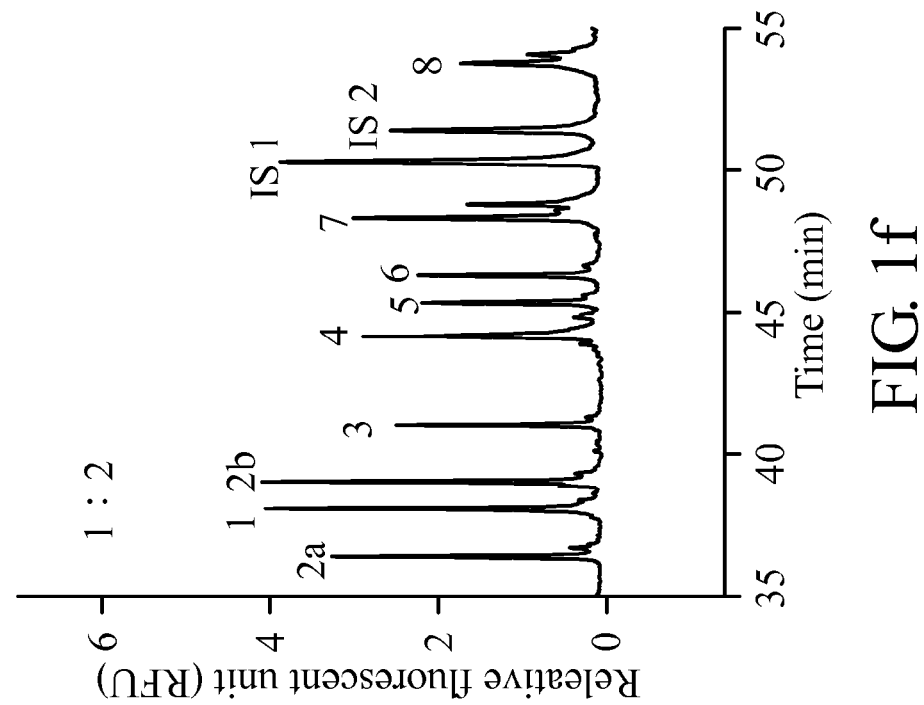
Figure 1F:
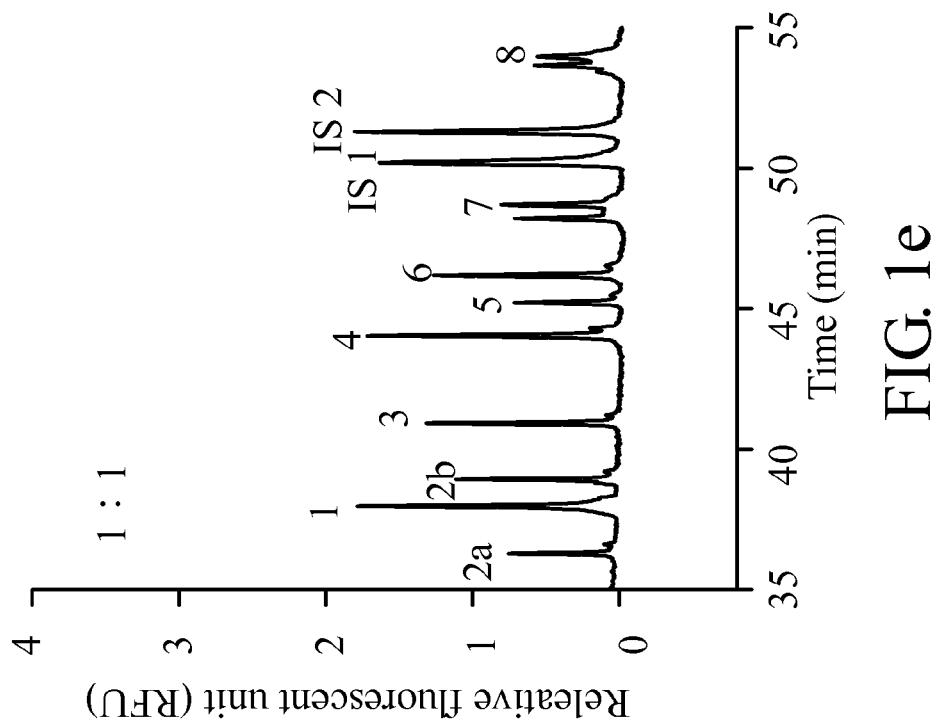

The following description is of the best-contemplated mode of carrying out the invention. This description is made for the purpose of illustrating the general principles of the invention and should not be taken in a limiting sense. The scope of the invention is best determined by reference to the appended claims.

The invention provides a method for determining a mutation in SMN gene. The method comprises: (a) providing a biological sample comprising a nucleotide containing an SMN gene; (b) providing primers for SMN exons 1, 2a, 2b, 3, 4, 5, 6, 7, and 8; (c) amplifying SMN exons 1, 2a, 2b, 3, 4, 5, 6, 7, and 8 by a universal multiplex PCR using the nucleotide as a template and the primers to obtain fragments of the SMN exons 1, 2a, 2b, 3, 4, 5, 6, 7, and 8; (d) labeling the fragments of the SMN exons 1, 2a, 2b, 3, 4, 5, 6, 7, and 8 by a fluorescent primer to obtain fluorescence-labeled exon fragments, and (e) analyzing the fluorescence-labeled exon fragments by a capillary electrophoresis. If ratios of SMN1/SMN2 in exon 7 and 8 are different, the result indicates that at least one gene conversion has occurred in the SMN gene. Additionally, if a crossed peak is observed in a capillary electrophoresis analysis, it indicates that at least one mutation has occurred in the SMN gene.

Firstly, a nucleotide containing SMN gene is provided. The nucleotide contains SMN exons 1, 2a, 2b, 3, 4, 5, 6, 7, and/or 8. Preferably, the nucleotide is a DNA fragment.

Primers for exons 1, 2a, 2b, 3, 4, 5, 6, 7, and 8 are provided. The primers of the invention include any kind of primer that is capable of amplifying exons 1, 2a, 2b, 3, 4, 5, 6, 7, and 8 by a polymerase chain reaction (PCR). The primers can be used in same or different PCR procedures, preferably, in same PCR procedures. In one embodiment, the primers for the SMN exons 1, 2a, 2b, 3, 4, 5, 6, 7, and 8 are SEQ ID NOs: 1-18, respectively, wherein the primers for the SMN exon 1 are SEQ ID NO:1 and 2, the primers for the SMN exon 2a are SEQ ID NOs:3 and 4, the primers for the SMN exon 2b are SEQ ID NOs:5 and 6, the primers for the SMN exon 3 are SEQ ID NOs:7 and 8, the primers for the SMN exon 4 are SEQ ID NOs:9 and 10, the primers for the SMN exon 5 are SEQ ID NO:11 and 12, the primers for the SMN exon 6 are SEQ ID NO:13 and 14, the primers for the SMN exon 7 are SEQ ID NO:15 and 16, and the primers for the SMN exon 8 are SEQ ID NO:17 and 18.

The SMN exons 1, 2a, 2b, 3, 4, 5, 6, 7, and 8 are amplified by a universal multiplex PCR using the nucleotide as a template and the primers to obtain fragments of the SMN exons 1, 2a, 2b, 3, 4, 5, 6, 7, and 8. Subsequently, the fragments of the SMN exons 1, 2a, 2b, 3, 4, 5, 6, 7, and 8 are labeled by a fluorescent primer to obtain fluorescence-labeled exon fragments. The fluorescent primer can be SEQ ID NO:21.

The universal multiplex PCR process includes two steps. In the first step, the SMN exons 1, 2a, 2b, 3, 4, 5, 6, 7, and 8 are amplified using the primers (SEQ ID NOs:1-18) to obtain fragments of the SMN exons 1, 2a, 2b, 3, 4, 5, 6, 7, and 8. In the second step, the fragments of the SMN exons 1, 2a, 2b, 3, 4, 5, 6, 7, and 8 then are amplified and labeled using a forward fluorescent primer (5') (SEQ ID NO:21) and reverse primer (3').

The amount of PCR cycles in the first step is not limited. A minimal amount of cycles may be used. The amount of cycles can be less than 10, preferably less than 2-5 to roughly amplify the SMN exons 1, 2a, 2b, 3, 4, 5, 6, 7, and 8. However, in the second step, the amount of PCR cycles preferably is more than 25 to produce enough amounts of fluorescence-labeled exon fragments. The PCR product can be directly analyzed by a capillary electrophoresis without any treatments.

The fluorescent molecules of the invention can be any suitable molecules. The fluorescent molecules includes, but is not limited to, Cy3, Cy5, FAM, HEX, TET, TAMRA, SyBr Green, GFP, or EGFP, etc. A suitable fluorescent molecule can bind to a universal primer to form the fluorescent primer, and the fluorescent primer is used to obtain the fluorescence-labeled exon fragments by PCR.

Finally, the fluorescence-labeled exon fragments are analyzed by a capillary electrophoresis. A gene which is constantly expressed can be used as an internal control for capillary electrophoresis quantitative analysis. The gene can be globin, actin, or BMP gene. If the ratios of SMN1/SMN2 in exon 7 and 8 are different, it indicates that at least one gene conversion has occurred in SMN gene. Additionally, if a crossed peak is observed in the capillary electrophoresis results, it indicates at least one mutation has occurred in SMN gene.

The invention also provides a method for diagnosing spinal muscular atrophy. The method comprises: (a) providing a biological sample comprising a nucleotide containing SMN gene, wherein the biological sample is obtained from a subject; (b) providing primers for SMN exons 1, 2a, 2b, 3, 4, 5, 6, 7, and 8; (c) amplifying SMN exons 1, 2a, 2b, 3, 4, 5, 6, 7, and 8 by a universal multiplex PCR using the nucleotide as a template and the primers to obtain fragments of the SMN exons 1, 2a, 2b, 3, 4, 5, 6, 7, and 8; (d) labeling the fragments of the SMN exons 1, 2a, 2b, 3, 4, 5, 6, 7, and 8 by a fluorescent primer to obtain fluorescence-labeled exon fragments, and (e) analyzing the fluorescence-labeled exon fragments by a capillary electrophoresis. If the ratios of SMN1/SMN2 in exon 7 and 8 are different, it indicates that the subject is susceptible to spinal muscular atrophy. Additionally, if a bifurcated peak is observed in the results of a capillary electrophoresis, it also indicates that the subject is susceptible to spinal muscular atrophy.

The "subject" of the invention refers to human or non-human mammal, e.g. a dog, a cat, a mouse, a rat, a cow, a sheep, a pig, a goat, or a primate, and expressly includes laboratory mammals, livestock, and domestic mammals. In one embodiment, the mammal may be a human; in others, the mammal may be a rodent, such as a mouse or a rat. In another embodiment, the subject is an animal model (e.g., a transgenic mouse model) of SMA. Alternatively, the subject is an SMA patient. The SMA patient can be homozygous or heterozygous for mutations in SMN1. The subject can be an adult, child, or fetus.

The "biological sample" of the invention can be isolated or collected from any source which contains genomic DNA, such as a blood sample, sample of amniotic fluid, sample of cerebrospinal fluid, or tissue sample from skin, muscle, buccal or conjunctival mucosa, placenta, gastrointestinal tract or other organs.

When the ratios of SMN1/SMN2 in exon 7 and 8 are different, it indicates that gene conversion has occurred in SMN gene. Additionally, the ratios of SMN1/SMN2 in exon 7 or 8 can be used to determine whether the subject is a healthy subject, SMA carrier, or SMA patient.

Generally, there are two copy of normal SMN1 in healthy subjects. For example, the SMN1/SMN2 ratio of healthy subjects may be 2:2, 2:1, 3:1, 2:0, 3:0, 3:2, 4:0, or 2:3, etc. Alternatively, there is only one copy of normal SMN1 in SMA carriers. For example, the SMN1/SMN2 ratio of SMA carriers may be 1:1, 1:2, 1:3 or 1:4, etc. However, there is no normal SMN1 in SMA patients. For example, the SMN1/SMN2 ratio of SMA patients may be 0:2, 0:3, or 0:4, etc. Thus, a subject can be determined by the ratio of SMN1/SMN2 to determine whether the subject is a healthy subject, SMA carrier, or SMA patient.

The SMN1/SMN2 ratios described above normally occur in most subjects. However, in a few subjects, mutations occur in SMN exon resulting in the loss of SMN gene function. For example, in one SMA patient, its SMN1/SMN2 ratio in SMN exon 7 and 8 are 1:2 and 1:3, respectively, and at least one mutation is observed in other SMN exons. This indicates that the SMA patient is due to the mutation of other SMN exons, but not SMN1 deletion.

In the invention, the capillary electrophoresis not only simultaneously analyzes the SMN1/SMN2 ratio in exon 7 and 8, but also determines the sequence difference and mutation location in other SMN exons. In addition, the PCR product can be directly analyzed by capillary electrophoresis without any treatment.

The invention further provides a kit for diagnosing susceptibility of spinal muscular atrophy. The kit comprises at least one primer pair selected from a group consisting of: SEQ ID NOs: 1-2, 3-4, 5-6, 7-8, 9-10, 11-12, 13-14, 15-16, and 17-18, and a user instruction.

Moreover, the kit of the invention further includes an internal control primer pair which is SEQ ID NOs: 19-20 or 19-22, and a fluorescent primer which is SEQ ID NO: 21.

EXAMPLES

Example 1

Diagnosis of Spinal Muscular Atrophy

Eleven primer pairs were provided in Example 1 to simultaneously amplify nucleotide fragments of SMN exons 1, 2a, 2b, 3, 4, 5, 6, 7, 8, and globin gene. The amount of nucleotide fragments of the globin gene was used as an internal control. The primer pairs are shown in Table 1.

TABLE 1 length and sequence in various primer pairs

| Genes | Primers | Length of primers | SEQ ID NO | Length of DNA fragment |
|---|---|---|---|---|
| SMN-exon 1 | Uni-5'-exon 1 | 41 | SEQ ID NO: 1 | 308 |
|  | 3'-exon 1 | 20 | SEQ ID NO: 2 |  |
| SMN-exon 2a | Uni-5'-exon 2a | 44 | SEQ ID NO: 3 | 274 |
|  | 3'-exon 2a | 23 | SEQ ID NO: 4 |  |
| SMN-exon 2b | Uni-5'-exon 2b | 44 | SEQ ID NO: 5 | 331 |
|  | 3'-exon 2b | 21 | SEQ ID NO: 6 |  |
| SMN-exon 3 | Uni-5'-exon 3 | 42 | SEQ ID NO: 7 | 382 |
|  | 3'-exon 3 | 23 | SEQ ID NO: 8 |  |
| SMN-exon 4 | Uni-5'-exon 4 | 42 | SEQ ID NO: 9 | 439 |
|  | 3'-exon 4 | 21 | SEQ ID NO: 10 |  |
| SMN-exon 5 | Uni-5'-exon 5 | 42 | SEQ ID NO: 11 | 474 |
|  | 3'-exon 5 | 20 | SEQ ID NO: 12 |  |
| SMN-exon 6 | Uni-5'-exon 6 | 43 | SEQ ID NO: 13 | 510 |
|  | 3'-exon 6 | 23 | SEQ ID NO: 14 |  |
| SMN-exon 7 | Uni-5'-exon 7 | 42 | SEQ ID NO: 15 | 577 |
|  | 3'-exon 7 | 21 | SEQ ID NO: 16 |  |
| SMN-exon 8 | Uni-5'-exon 8 | 46 | SEQ ID NO: 17 | 809 |
|  | 3'-exon 8 | 20 | SEQ ID NO: 18 |  |
| β-globin (IS1) | Uni-5'-globin | 41 | SEQ ID NO: 19 | 715 |
|  | 3'-globin 1 | 28 | SEQ ID NO: 20 |  |
| B-globin (IS2) | Uni-5'-globin | 41 | SEQ ID NO: 19 | 763 |
|  | 3'-globin 2 | 23 | SEQ ID NO: 22 |  |
| fluorescent primer | 5'-FAM | 17 | SEQ ID NO: 21 |  |

All primer pairs were classified into two (A and B) groups. The primer pairs had the same PCR procedures in the same group. The PCR procedures of two groups are shown in Table 2.

TABLE 2

Reactant concentration in PCR reaction

| Group A | | Group B | |
|---|---|---|---|
| DNA | 100 ng | DNA | 100 ng |
| dNTP | 200 μg | dNTP | 200 μM |
| 10 × PCR buffer | 2.5 μl | 10 × PCR buffer | 2.5 μl |
| Uni-5'-exon 1 | 0.004 μM | Uni-5'-exon 3 | 0.012 μM |
| Uni-5'-exon 2a | 0.006 μM | Uni-5'-exon 4 | 0.012 μM |
| Uni-5'-exon 2b | 0.012 μM | Uni-5'-exon 6 | 0.008 μM |
| Uni-5'-exon 5 | 0.012 μM | Uni-5'-exon 8 | 0.02 μM |
| Uni-5'-exon 7 | 0.02 μM | Uni-5'-globin | 0.006 μM |
| Uni-5'-globin | 0.012 μM | 3'-exon 3 | 0.08 μM |
| 3'-exon 1 | 0.08 μM | 3'-exon 4 | 0.16 μM |
| 3'-exon 2a | 0.06 μM | 3'-exon 6 | 0.08 μM |
| 3'-exon 2b | 0.16 μM | 3'-exon 8 | 0.16 μM |
| 3'-exon 5 | 0.12 μM | 3'-globin-2 | 0.06 μM |
| 3'-exon 7 | 0.28 μM | 5'-FAM | 0.4 μM |
| 3'-globin-1 | 0.16 μM | Taq | 0.5 unit |
| 5'-FAM | 0.4 μM |  |  |
| Taq | 0.5 unit |  |  |
| Total volume | 25 μl | Total volume | 25 μl |

The PCR reaction was divided into two steps. In the first step, the PCR procedures were 1 cycle of 95° C. for 10 min, and 3 cycles of 95° C. for 45 sec and 60° C. for 2 min. The forward and reverse primers (as shown in Table 1) were used to amplify the SMN gene. Since the primer contains a conserved sequence, all amplified SMN gene fragments had the conserved sequence. In the second step, the universal-5'-FAM primer and a reverse primer were used to amplify and label the SMN gene fragments. After PCR reaction, the fluorescence-labeled SMN gene fragments were directly analyzed by capillary electrophoresis without any treatment. The PCR procedures of the second step were 25 cycles of 95° C. for 45 sec, 50° C. for 1.5 min and 72° C. for 1 min; and 1 cycle of 72° C. for 10 min.

In the capillary electrophoresis, Beckman P/ACE MDQ system, a laser induced fluorescence (LIF), and a DB-17 capillary were used. The LIF has an excitation wavelength of 488 nm and emission wavelength of 520 nm. The internal temperature of DB-17 was about 15° C.

Figure 1H:
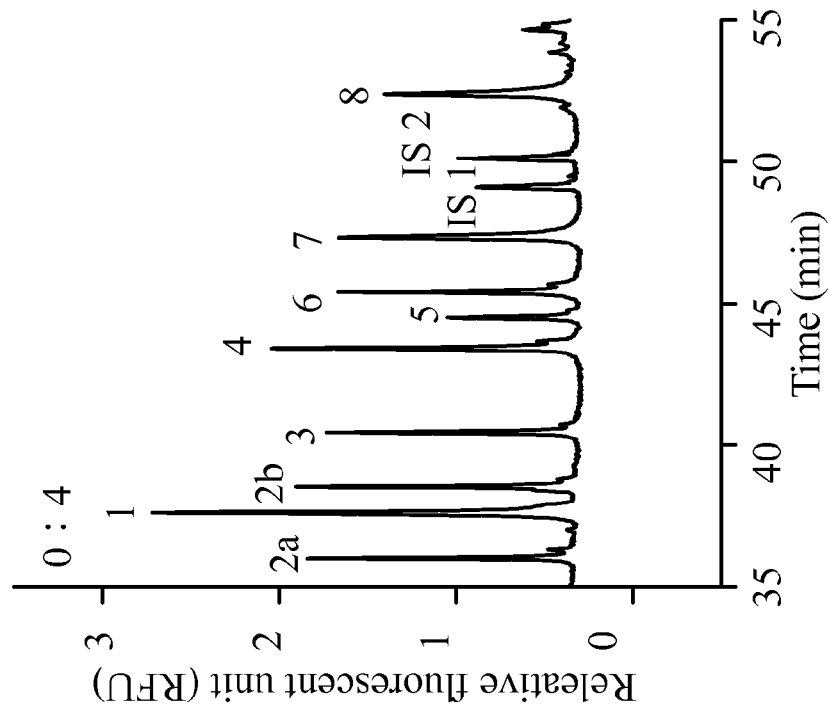
Figure 1G:
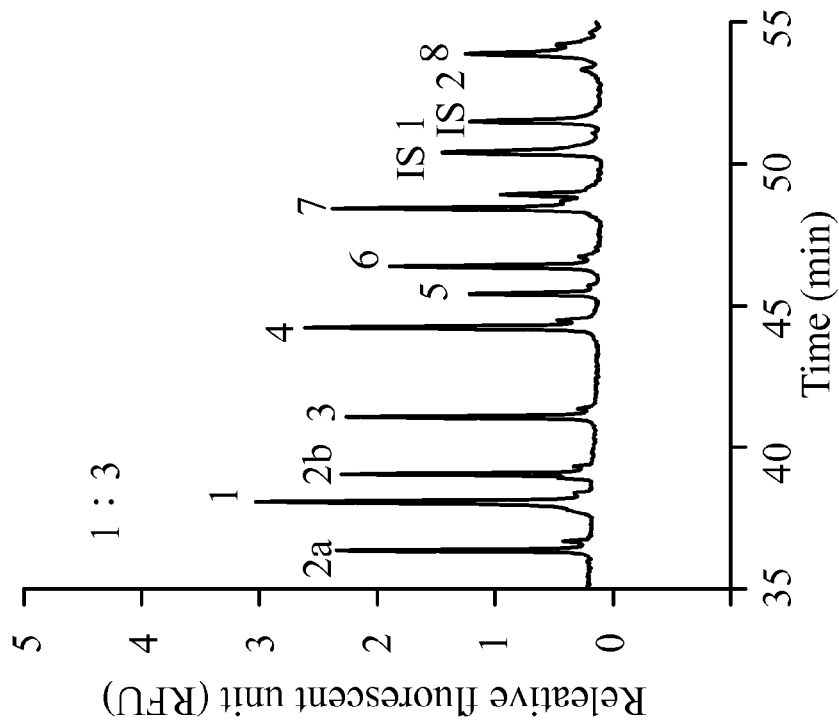

After capillary electrophoresis analysis, the nucleotide fragments of SMN exons 1, 2a, 2b, 3, 4, 5, 6, 7, and 8 were quantified. The β-globin (IS1) was used to quantify the SMN1/SMN2 ratio in exon 7, and the β-globin (IS2) was used to quantify the SMN1/SMN2 ratio in exon 8. FIGS. 1a-1h show the SMN1/SMN2 ratios of 4:0 (FIG. 1a), 3:1 (FIG. 1b), 2:1 (FIG. 1c), 2:2 (FIG. 1d), 1:1 (FIG. 1e), 1:2 (FIG. 1f), 1:3 (FIG. 1g), and 0:4 (FIG. 1h).

Figure 2:
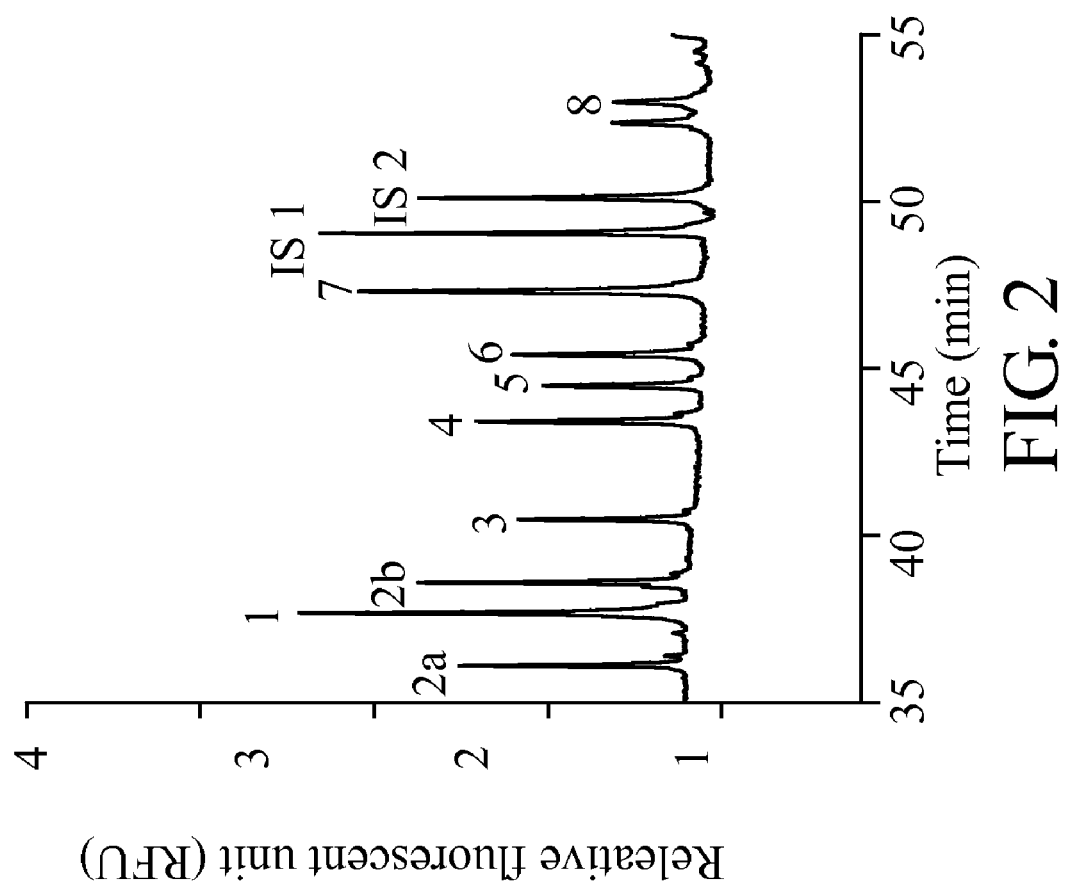
FIG. 2 shows a result of a capillary electrophoresis analysis, wherein the SMN1/SMN2 in exon 7 and 8 are 0:2 and 1:1, respectively.

When SMN1/SMN2 ratios in exon 7 and exon 8 are different, it indicates that the gene conversion has occurred in SMN gene. Referring to FIG. 2, the SMN1/SMN2 ratio in exon 7 was 0:2 and the SMN1/SMN2 ratio in exon 8 was 1:1. The results indicated the subject was an SMA patient, and one copy of SMN2 in exon 8 was conversed to SMN1.

Figure 3A:
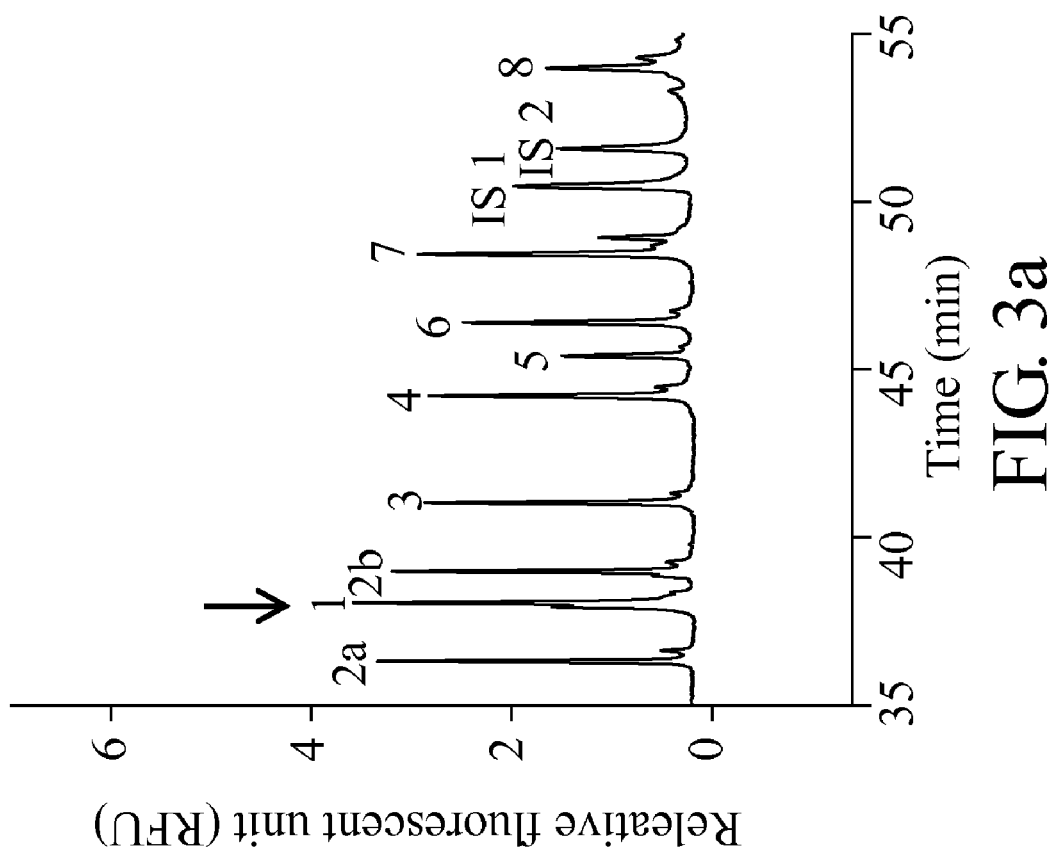

In addition to the quantitative analysis of SMN1/SMN2 in exons 7 and 8, the point mutation or difference in other SMN exons was also determined. FIGS. 3a-3b show results of a capillary electrophoresis analysis and DNA sequencing of an SMA patient bearing one copy of SMN1 and a c.22_23insA mutation in exon 1. FIGS. 4a-4b show capillary electrophoresis results and DNA sequencing of a healthy subject. When comparing FIGS. 3a and 4a, a crossed peak was observed in exon 1, and the location of mutation was determined by the sequencing data of FIGS. 3b and 4b. Referring to FIGS. 3a-3b, SMN1/SMN2 ratios in exon 7 and exon 8 were 1:3. However, an intragenic mutation was observed in exon 1, and the location of the intragenic mutation was located by sequencing data. Accordingly, the results indicated that the SMA patient had one copy of SMN1 due to a gene mutation in an SMN exon 1.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A kit for assaying a sample from a subject to detect a susceptibility of spinal muscular atrophy, comprising:
   at least one primer pair selected from the group consisting of: SEQ ID NOs: 1-2, 3-4, 5-6, 7-8, 9-10, 11-12, 13-14, 15-16, and 17-18, and
   a user instruction.

2. The kit as claimed in claim 1, further comprising an internal control primer pair, wherein the internal control primer pair is SEQ ID NOs: 19-20 or 19-22.

3. The kit as claimed in claim 1, further comprising a fluorescent primer, wherein the fluorescent primer is SEQ ID NO: 21.

* * * * *

SEQUENCE LISTING

<160> NUMBER OF SEQ ID NOS: 22

<210> SEQ ID NO 1
<211> LENGTH: 41

```
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 1
ataagtgacg tactagcaac gccacaaatg tgggagggcg a                           41

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 2
gggtgctgag agcgctaata                                                  20

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 3
ataagtgacg tactagcaac ggtttcctgt ggctttattt agga                       44

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 4
cgagaaaata agaaaacgac taa                                              23

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 5
ataagtgacg tactagcaac gaaaagagaa aataggtgct ttct                       44

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 6
acactattaa ataaggacta a                                                21

<210> SEQ ID NO 7
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      nucleotide

<400> SEQUENCE: 7
ataagtgacg tactagcaac gagcctttct cattacatca tt                            42

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 8
tgaatttttt tttttttgta tcc                                                 23

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 9
ataagtgacg tactagcaac gccttataac aaaaacctgc at                            42

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 10
aaaagttaac tggataaatc t                                                   21

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 11
ataagtgacg tactagcaac gaaggaaatg agaaaaatcc ag                            42

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 12
ttgggactac aagagcactg                                                     20

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
``` nucleotide

<400> SEQUENCE: 13
ataagtgacg tactagcaac gctccaaatg ctagctatgt taa                         43

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 14
gagagaagca agtagtattt tat                                               23

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 15
ataagtgacg tactagcaac gtgtcttgtg aaacaaaatg ct                          42

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 16
aaaccatgtc ctctgtggac a                                                 21

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 17
ataagtgacg tactagcaac ggaacattta aaaagttcag atgtta                      46

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 18
tttaagacac tctaacactt                                                   20

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
      nucleotide

```
<400> SEQUENCE: 19
ataagtgacg tactagcaac gactgactct ctctgcctat t                    41

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 20
cccataaata tgtataatga ttatgtat                                   28

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 21
gtgacgtact agcaacg                                               17

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 22
ccctgatttg gtcaatatgt gta                                        23
```